(12) United States Patent
Yu et al.

(10) Patent No.: US 11,376,163 B2
(45) Date of Patent: Jul. 5, 2022

(54) DEVICES, SYSTEMS, AND METHODS FOR VISION RESTORATION

(71) Applicant: Board of Trustees of the University of Illinois, Chicago, IL (US)

(72) Inventors: Charles Yu, San Francisco, CA (US);
Mark Rosenblatt, Chicago, IL (US);
Songbin Gong, Champaign, IL (US);
Sarah Yoonji Shim, Champaign, IL (US)

(73) Assignee: Board of Trustees of the University of Illinois, Chicago, IL (US)

( * ) Notice: Subject to any disclaimer, the term of this patent is extended or adjusted under 35 U.S.C. 154(b) by 169 days.

(21) Appl. No.: 16/810,603

(22) Filed: Mar. 5, 2020

(65) Prior Publication Data
US 2020/0197223 A1    Jun. 25, 2020

Related U.S. Application Data

(63) Continuation of application No. PCT/US2018/050603, filed on Sep. 12, 2018.
(Continued)

(51) Int. Cl.
*A61F 2/14* (2006.01)
*A61F 9/08* (2006.01)
(Continued)

(52) U.S. Cl.
CPC ............. *A61F 9/08* (2013.01); *A61F 2/14* (2013.01); *H04N 9/31* (2013.01); *A61F 2250/0002* (2013.01); *G02B 5/30* (2013.01)

(58) Field of Classification Search
CPC .. A61F 2/14; A61F 9/08; A61F 2/1451; A61F 2/16; A61F 2250/0002; A61F 2250/0053; A61F 2250/0091
See application file for complete search history.

(56) References Cited

U.S. PATENT DOCUMENTS 4,073,015 A * 2/1978 Peyman ................ A61F 2/1608
623/6.5
4,865,601 A 9/1989 Caldwell et al.
(Continued)

FOREIGN PATENT DOCUMENTS

WO    WO 2019/055477    3/2019

OTHER PUBLICATIONS

Gain et al., "Global Survey of Corneal Transplantation and Eye Banking" *JAMA Ophthalmology* vol. 134, No. 2, pp. 167-173, 2016.
(Continued)

*Primary Examiner* — Paul B Prebilic
(74) *Attorney, Agent, or Firm* — Levine Bagade Han LLP

(57) ABSTRACT

Disclosed are devices, systems, and methods for restoring vision to a subject. In one embodiment, the vision restoration device comprises a projector configured to project one or more digital images onto a central retina of the subject and one or more lenses coupled to the projector and configured to focus the one or more digital images. The vision restoration device can also comprise an extraocular component configured to be implanted within the subject and comprising one or more processors programmed to execute instructions stored in a memory to wirelessly receive the one or more digital images from an extracorporeal device. The intraocular projection component can be connected or coupled to the extraocular component by a trans-scleral communication wire configured to cross the sclera of the eye. The trans-scleral communication wire is configured to transmit digital data between the extraocular component and the intraocular projection component.

18 Claims, 11 Drawing Sheets

Related U.S. Application Data

(60) Provisional application No. 62/569,794, filed on Oct. 9, 2017, provisional application No. 62/558,594, filed on Sep. 14, 2017.

(51) Int. Cl.
  *H04N 9/31* (2006.01)
  *G02B 5/30* (2006.01)

(56) References Cited

U.S. PATENT DOCUMENTS

| | | | |
|---|---|---|---|
| 5,030,230 A | 7/1991 | White | |
| 5,653,751 A | 8/1997 | Samiy et al. | |
| 6,197,057 B1 | 3/2001 | Peyman et al. | |
| 6,203,538 B1 | 3/2001 | Peyman | |
| 6,387,126 B1 | 5/2002 | Cumming | |
| 7,130,700 B2 | 10/2006 | Gardeski et al. | |
| 7,551,590 B2 | 6/2009 | Haller et al. | |
| 7,727,277 B2 | 6/2010 | Aharoni et al. | |
| 8,092,526 B2 | 1/2012 | Daxer | |
| 8,377,120 B2 | 2/2013 | Lipshitz et al. | |
| 9,302,107 B2 | 4/2016 | Lauritzen et al. | |
| 9,744,076 B2 | 8/2017 | da Silva Curiel et al. | |
| 2002/0161437 A1 | 10/2002 | Zhou et al. | |
| 2004/0117011 A1 | 6/2004 | Aharoni et al. | |
| 2005/0015120 A1 | 1/2005 | Seibel et al. | |
| 2008/0046033 A1 | 2/2008 | McClure et al. | |
| 2010/0057166 A1 | 3/2010 | Ahuja et al. | |
| 2010/0165660 A1 | 7/2010 | Weber et al. | |
| 2010/0171922 A1 | 7/2010 | Sessner et al. | |
| 2011/0152969 A1 | 6/2011 | Zehnder et al. | |
| 2013/0033610 A1 | 2/2013 | Osborn | |
| 2014/0184384 A1 | 7/2014 | Zhu et al. | |
| 2014/0371852 A1 | 12/2014 | Aharoni et al. | |
| 2015/0366656 A1* | 12/2015 | Wortz | A61F 2/15 623/6.22 |
| 2016/0331968 A1 | 11/2016 | Greenberg et al. | |
| 2017/0189170 A1 | 7/2017 | Haddock et al. | |
| 2018/0353332 A1* | 12/2018 | Saini | A61F 2/1624 |

OTHER PUBLICATIONS

Waldock et al., "Corneal transplantation: how successful are we?" *Br J Ophthalmol* vol. 84, pp. 813-815, 2000.

* cited by examiner

DEVICES, SYSTEMS, AND METHODS FOR VISION RESTORATION

CROSS-REFERENCE TO RELATED APPLICATIONS

This application is a continuation of International Application No. PCT/US2018/050603 filed Sep. 12, 2018, which claims the benefit of priority to U.S. Provisional Patent Application No. 62/558,594, filed on Sep. 14, 2017, and U.S. Provisional Patent Application No. 62/569,794, filed on Oct. 9, 2017, the contents of which are hereby incorporated by reference in their entireties.

TECHNICAL FIELD

The present disclosure relates generally to the field of ophthalmology and, more specifically, to implantable devices, systems, and methods for vision restoration.

BACKGROUND

The cornea is the normally clear anterior portion of the eye. When the cornea is functioning properly, it allows light into the eye and helps focus this onto the retina, providing vision. When damaged, the clear tissue of the cornea becomes opaque and the patient loses visual function, resulting in a condition known as corneal opacity. Corneal opacity can be caused by injuries (e.g., chemical exposure), infections (e.g., corneal ulcers or trachoma), and inherited genetic conditions or dystrophies which develop later in life (e.g., corneal dystrophies such as Fuchs' dystrophy). While degenerative conditions worsen gradually, injuries and infections often develop quickly and require the patient to seek a solution as soon as possible to carry on with their lives. Moreover, since industrial accidents are a major cause of corneal injury, corneal problems affect a younger population than other eye conditions such as cataracts, macular degeneration, and glaucoma. Such younger patients also have a much longer lifespan once their vision has been impaired.

While corneal transplantation can be used to restore clarity as long as certain intraocular tissues remain intact, such procedures are high risk, have a high failure rate, and there is a limited availability of corneas worldwide due to donor shortages. For example, one study has reported that the success rate of routine (i.e., non-high-risk) transplantations is approximately 62% at 10 years after transplantation and the success rate of high-risk transplantations drops to less than 35% at 10 years after transplantation. See Waldock, A., and S. D. Cook. "Corneal transplantation: how successful are we?" British Journal of Ophthalmology 84.8 (2000): 813-815. Corneal transplants can fail due to rejection of the transplanted tissue, infection by bacteria or viruses, or when blood vessels have grown into the diseased or damaged cornea prior to transplantation. Moreover, a study conducted using data collected from more than one hundred countries showed that an estimated 12.7 million people are on corneal transplant waiting lists. See Gain, Philippe, et al. "Global survey of corneal transplantation and eye banking." JAMA ophthalmology 134.2 (2016): 167-173.

Furthermore, while retinal artificial visions systems such as the Argus™ II and Alpha IMS systems have been used to restore vision to patients with outer retina degeneration. These devices are not designed for use with patients with intact outer retinas such as those suffering solely from cornea related blindness. Moreover, patients who have undergone such procedures must use eye drops daily for up to five years, must see an ophthalmologist every month for one year (then every three months for 10 years), and must have access to an ophthalmologist within 24 hours if an infection occurs. In addition, the cost of implanting such a system can add up to almost $20,000 to $30,000.

Therefore, improved devices, systems, and methods are needed to treat blindness caused by corneal degeneration that are robust and long-lasting. Such devices, systems, and methods should be cost-effective compared to current artificial systems, require less time and effort to implant, and could serve as either a short-term solution to patients awaiting a corneal transplant or a long-term solution that bypasses transplantation altogether.

SUMMARY

Disclosed herein are implantable devices, systems, and methods for vision restoration. In one embodiment, a vision restoration device is disclosed. The vision restoration device can comprise an intraocular projection component configured to be implanted within an eye of the subject. The intraocular projection component can comprise a projector configured to project one or more digital images onto a central retina of the subject.

In some embodiments, the projector can comprise a projector housing comprising a front housing interior wall and a back housing interior wall. The projector housing can be substantially cuboid. The projector housing can be made in part of at least one of medical grade poly(methyl methacrylate) (PMMA), medical grade silicone, and medical grade polyvinyl chloride (PVC).

The projector housing can further comprise a front housing comprising a front housing interior wall and a back housing comprising a back housing interior wall. The projector housing can comprise a housing cavity when the front housing is coupled to the back housing. The housing cavity can be surrounded by interior housing walls and the interior housing walls can be coated by a light-sealing coating. In one embodiment, the light-sealing coating can comprise a silver-colored coating. In an alternative embodiment, the light-sealing coating can comprise a black-colored coating.

The projector can also comprise an electronic display housed within the projector housing and configured to display the digital image. In one embodiment, the electronic display can be a liquid-crystal display (LCD) display.

The projector can further comprise a first polarizing filter positioned in between the electronic display and the front housing interior wall within the projector housing. The projector can also comprise a light emitting component configured to generate and direct light at the electronic display. At least part of the light emitting component can be housed within the projector housing. The light emitting component can be a light reflecting enclosure housing one or more light-emitting diodes (LEDs).

The projector can also comprise a light diffuser configured to diffuse the light produced by the light emitting component. The light diffuser can be housed within the projector housing. A second polarizing filter can be positioned in between the light diffuser and the electronic display within the projector housing.

The intraocular projection component can also comprise one or more lenses coupled to the projector and configured to focus the one or more digital images. In some embodiments, the lens can be a plano-convex lens having a convex side and a substantially planar side. The convex side of the plano-convex lens can be positioned anterior to the substantially planar side when the intraocular projection component is implanted within the eye of the subject. In these and other embodiments, the intraocular projection component can comprise two or more lenses positioned in series when coupled to the projector. In some embodiments, at least one of the one or more lenses can be an adjustable lens such that the adjustable lens is translatable relative to the projector.

In certain embodiments, the projector housing can comprise a projector lens shroud protruding from a front housing of the projector housing. The one or more lenses can be coupled to the projector lens shroud.

In some embodiments, the projector can have a width dimension ranging from about 1.0 mm to about 11.0 mm, a length dimension ranging from about 1.0 mm to about 11.0 mm, and a depth dimension ranging from about 1.0 mm to about 11.0 mm. In these and other embodiments, the one or more lenses can each have a lens diameter and a lens depth dimension. The lens diameter can range from about 1.0 mm to about 10.0 mm and the lens depth dimension can range from about 1.0 mm to about 3.0 mm.

In one embodiment, the intraocular projection component can comprise two or more scleral haptics coupled to the projector. The scleral haptics can be configured to secure the intraocular projection component to a sclera of the subject. In other embodiments, the intraocular projection component can comprise two or more haptics comprising suture openings. The suture openings can be configured to allow the intraocular projection component to be secured to the eye using sutures.

The vision restoration device can further comprise an extraocular component configured to be implanted within the subject. The extraocular component can comprise one or more processors programmed to execute instructions stored in a memory to wirelessly receive the one or more digital images from an extracorporeal device.

In some embodiments, the extracorporeal device can comprise a digital camera and a wireless communication processor. The digital camera can be configured to capture the one or more digital images and the wireless communication processor can be programmed to execute instructions stored in a memory to wirelessly transmit the one or more digital images to the extraocular component. In other embodiments, the extracorporeal device can be at least one of a smartphone, a laptop, and a tablet computer.

The extraocular component can also comprise a wireless power and data receiver coil. The wireless power and data receiver coil can be configured to receive power wirelessly from a wireless power and data transmitter coil of the extracorporeal device positioned in proximity to the wireless power and data receiver coil. In some embodiments, the extraocular component can comprise a rechargeable battery configured to be recharged using power received wirelessly via the wireless power and data receiver coil.

The vision restoration device can further comprise a trans-scleral communication wire connecting or electrically coupling the intraocular projection component to the extraocular component. The trans-scleral communication wire can be configured to transmit digital data between the extraocular component and the intraocular projection component. The trans-scleral communication wire can comprise a first wire segment coupled to the intraocular projection component, a second wire segment coupled to the extraocular component, and a wire connector connecting the first wire segment to the second wire segment. The wire connector can be configured to allow the first wire segment to be detached from the second wire segment.

The trans-scleral communication wire can be made in part of a plurality of conductive wires covered by a biocompatible polymeric material. In some embodiments, at least one of the conductive wires can be made in part of at least one of copper, gold, and silver. The biocompatible polymeric material can be made in part of at least one of medical grade silicone, medical grade thermoplastic elastomers (TPEs), medical grade thermoplastic polyurethanes (TPUs), and medical grade polyvinyl chlorides (PVCs). At least a part of the trans-scleral communication wire can be coupled to an electronic display within the projector.

In another embodiment, a vision restoration system is disclosed. The vision restoration system can comprise an extracorporeal device comprising a wearable support structure configured to be worn by a subject, a digital camera coupled to the wearable support structure, and a processor housing comprising a camera processor and a wireless communication processor.

The wearable support structure can be configured to be worn in proximity to the eyes of the subject. In one embodiment, the wearable support structure can be an eyeglass frame. In another embodiment, the wearable support structure can be a headband configured to be worn on a head of the subject.

The extracorporeal device can further comprise a power supply coupled to the wearable support structure and a camera processor programmed to execute instructions stored in a camera memory to instruct the digital camera to capture one or more digital images.

The extracorporeal device can also comprise a wireless power and data transmitter coil housed within a coil housing coupled to the wearable support structure. The wireless power and data transmitter coil can be coupled to a portable power supply;

The vision restoration system can also comprise an extraocular component configured to wirelessly receive the one or more digital images captured by the digital camera from the extracorporeal device. The extraocular component can be configured to be implanted within the subject. The extraocular component can also comprise a wireless power and data receiver coil configured to receive power wirelessly via the wireless power and data transmitter coil.

The vision restoration system can also comprise an intraocular projection component configured to be implanted within an eye of the subject. The intraocular projection component can comprise a projector configured to project the one or more digital images received by the extraocular component onto a central retina of the subject and one or more lenses coupled to the projector configured to focus the one or more digital images.

The vision restoration system can further comprise a trans-scleral communication wire connecting the extraocular component to the intraocular projection component. The trans-scleral communication wire can be configured to transmit digital data between the extraocular component and the intraocular projection component.

In another embodiment, a method of restoring vision to a subject is disclosed. The method can comprise implanting an intraocular projection component within an eye of a subject by securing the intraocular projection component to an anterior portion of the eye. The intraocular projection component can be secured to the anterior portion of the eye using two or more scleral haptics. The intraocular projection component can also be secured to the sclera of the eye using sutures.

In one embodiment, implanting the intraocular projection component within the eye of a subject can comprise first removing a cornea of the subject and then replacing the cornea of the subject with another cornea, an artificial cornea, or a combination thereof after the intraocular projection component is implanted within the eye. Alternatively, the method can comprise suturing the cornea of the subject back onto the eye after the intraocular projection component is implanted within the eye.

The method can also comprise implanting an extraocular component subcutaneously within the subject. The extraocular component can be connected to the intraocular projection component by a trans-scleral communication wire. The method can further comprise receiving one or more digital images wirelessly using one or more processors within the extraocular component from an extracorporeal device. The one or more processors can be programmed to execute instructions stored in a memory of the extraocular component to receive the one or more digital images and store the digital images in the memory of the extraocular component. The method can also comprise projecting the one or more digital images onto a central retina in a posterior portion of the eye using a projector of the intraocular projection component. The one or more digital images can be received by the intraocular projection component from the extraocular component via the trans-scleral communication wire.

In some embodiments, the one or more digital images can be captured using the extracorporeal device. The one or more digital images can then be wirelessly transmitted to the extraocular component using a short-range communication protocol.

The method can further comprise focusing the one or more digital images projected onto the central retina of the subject using one or more plano-convex lenses of the intraocular projection component. In one embodiment, the method can also comprise adjusting the position of at least one of the plano-convex lenses by translating the plano-convex lens in at least one of an anterior direction and a posterior direction relative to a projector of the intraocular projection component.

The extraocular component can also comprise a wireless power and data receiver coil. The method can also comprise transferring power wirelessly to the wireless power and data receiver coil using a wireless power and data transmitter coil within an extracorporeal device.

In one embodiment, the method can comprise removing a lens capsule of the subject prior to securing the intraocular projection component and implanting the intraocular projection component in place of the lens capsule. In an alternative embodiment, the method can comprise implanting the intraocular projection component within the lens capsule of the eye. In a further embodiment, the method can comprise implanting the intraocular projection component within the eye of the subject by securing the intraocular projection component to the anterior chamber of the eye. In yet another embodiment, the method can comprise securing the intraocular projection component to the cornea of the subject using sutures.

In these and other embodiments, the method can comprise implanting the extraocular component subcutaneously in a retroauricular region of the subject. In an alternative embodiment, the method can also comprise implanting the extraocular component within an orbit of the subject. In yet another embodiment, the method can also comprise implanting the extraocular component subcutaneously in proximity to a temple of the subject. In another embodiment, the method can further comprise securing the extraocular component to a surface of the eye.

DETAILED DESCRIPTION

Figure 1:
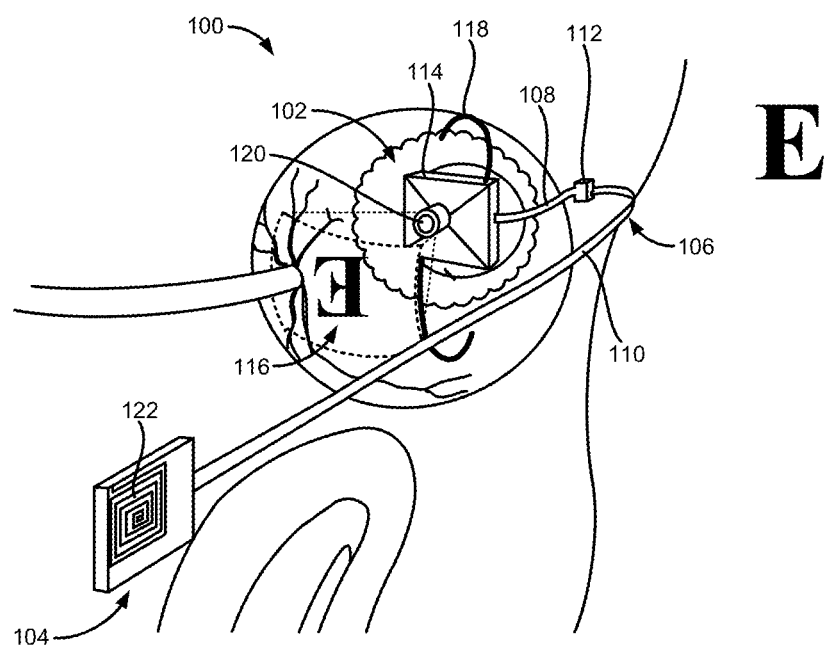
FIG. 1 illustrates an embodiment of a vision restoration device implanted within a subject.

FIG. 1 illustrates an embodiment of a vision restoration device 100 implanted within a subject. In some embodiments, the subject can be a human subject. In other embodiments, the subject can be a non-human animal subject such as a canine subject, a feline subject, or a non-human primate subject. The vision restoration device 100, along with the systems and methods disclosed herein, can be used to restore vision to a subject suffering loss of visual function. For example, the vision restoration device 100 disclosed herein can be used to restore vision to a subject afflicted with corneal opacity. The vision restoration device 100, along with the systems and methods disclosed herein, can also be used to restore vision to a subject determined to be unsuited for corneal transplantation or awaiting a cornea transplant.

The vision restoration device 100 can comprise an intraocular projection component 102, an extraocular component 104, and a trans-scleral communication wire 106 connecting the intraocular projection component 102 to the extraocular component 104. The intraocular projection component 102 can be configured to be implanted within an eye of the subject. The extraocular component 104 can be configured to be implanted subcutaneously in various locations in proximity to the eye or the ear of the subject. For example, as shown in FIG. 1, the extraocular component 104 can be implanted subcutaneously in a retroauricular region of the subject. As will be discussed in more detail in the following sections, the extraocular component 104 can also be secured to an outer surface of the eye.

The trans-scleral communication wire 106 can be configured to transmit digital data between the extraocular component 104 and the intraocular projection component 102. The trans-scleral communication wire 106 can cross or extend through the sclera 200 (see FIG. 2) of the eye when the intraocular projection component 102 is implanted within the eye of the subject and the extraocular component 104 is implanted outside of the eye or on an exterior surface of the eye. The trans-scleral communication wire 106 can comprise a first wire segment 108 coupled to the intraocular projection component 102, a second wire segment 110 coupled to the extraocular component 104, and a wire connector 112 connecting the first wire segment 108 to the second wire segment 110. At least a portion of the first wire segment 108 can extend into or penetrate through the sclera 200 (see FIG. 2) of the subject. The wire connector 112 can be configured to allow the second wire segment 110 to be detached from the first wire segment 108. Detaching the second wire segment 110 from the first wire segment 108 can allow the extraocular component 104 to be repaired or replaced without having to disturb the intraocular projection component 102. Moreover, the wire connector 112 (and breaking the trans-scleral communication wire 106 into two segments) can allow the intraocular projection component 102 to be implanted in a first procedure and the extraocular component 104 to be implanted in a second procedure. The first wire segment 108 and the second wire segment 110 can then be attached or connected together using the wire connector 112 during or after the second procedure.

Figure 2:
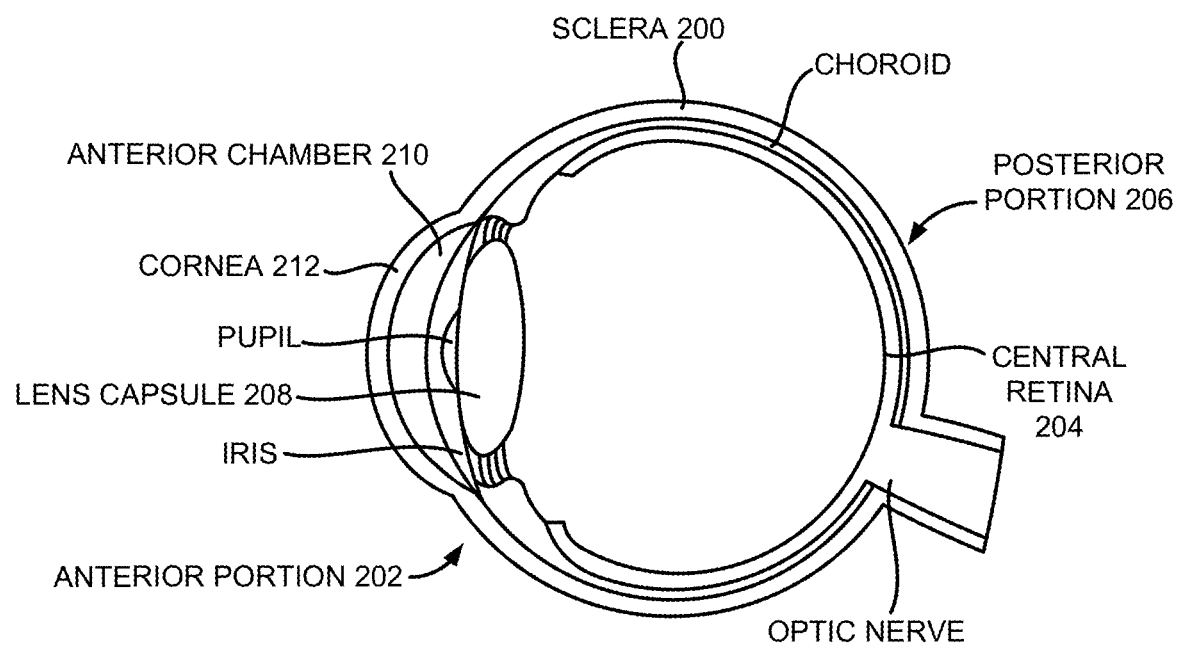
FIG. 2 illustrates the anatomy of a human eye.

The intraocular projection component 102 can comprise a projector 114 configured to be implanted within the eye and secured or affixed to an anterior portion 202 (see FIG. 2) of the eye. The projector 114 can also be configured to project one or more digital images 116 within the eye. In one embodiment, the projector 114 can be configured to project one or more digital images 116 onto a central retina 204 (see FIG. 2) of the subject. As shown in FIG. 2, the central retina 204 is in a posterior portion 206 of the eye.

As shown in FIG. 1, the intraocular projection component 102 can also comprise two or more securing haptics 118 coupled to the projector 114 and configured to secure the intraocular projection component 102 to the eye. In one embodiment, the securing haptics 118 can be scleral haptics configured to secure the intraocular projection component 102 to the sclera 200 of the subject. Although two securing haptics 118 are shown in FIG. 1, it is contemplated by this disclosure that between three and twelve haptics (arranged uniformly around the projector 114) can be used to secure the intraocular projection component 102 to the eye.

The intraocular projection component can also comprise one or more lenses 120 coupled to the projector 114 and configured to focus the one or more digital images 116. The lenses 120 will be discussed in more detail in the following sections.

The projector 114 can display and project one or more digital images 116 stored in a memory of the extraocular component 104. The extraocular component 104 can comprise one or more processors programmed to execute instructions stored in the memory to wirelessly receive the digital images 116 from an extracorporeal device 1000 (see FIGS. 10A, 10B, and 10C). The one or more processors of the extraocular component 104 can also control the display and projection of the digital images 116 by the projector 114.

As shown in FIG. 1, the extraocular component 104 can also comprise a wireless power and data receiver coil 122. The wireless power and data receiver coil 122 can be configured to receive power wirelessly from a wireless power and data transmitter coil 1008 (see FIGS. 10A and 10B) of the extracorporeal device 1000. The extracorporeal device 1000 will be discussed in more detail in the following sections.

FIG. 2 illustrates the anatomy of a human eye. FIG. 2 is provided as a reference for understanding the positioning of certain components of the vision restoration device 100 within the eye.

Figure 3A:
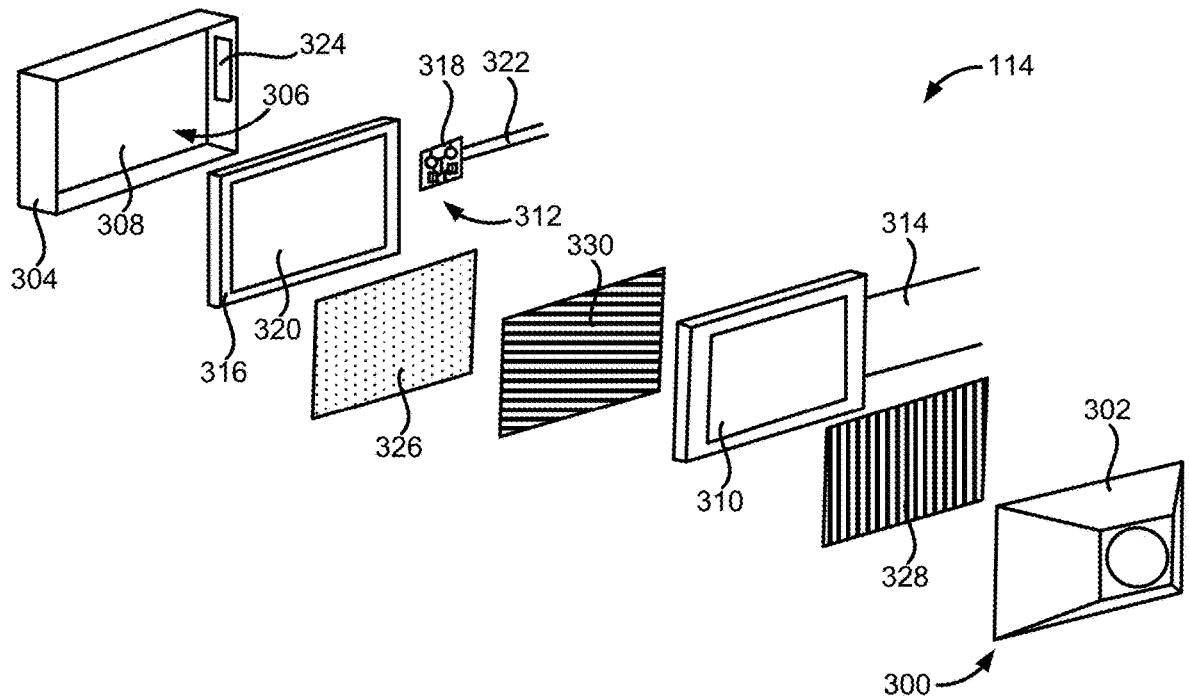
FIG. 3A illustrates an exploded view of an embodiment of a projector of the vision restoration device.

FIG. 3A illustrates an exploded view of an embodiment of a projector 114 of the intraocular projection component 102. The projector 114 can comprise a projector housing 300 comprising a front housing 302 and a back housing 304. The front housing 302 and the back housing 304 can define a housing cavity 306 when the front housing 302 is coupled to the back housing 304. The front housing 302 can be coupled to the back housing 304 by adhesives, an interference fit, heat sealing or other polymer welding techniques, or a combination thereof.

As shown in FIG. 3A, the front housing 302 can be substantially shaped as a truncated rectangular pyramid. In other embodiments, the front housing 302 can be substantially shaped as a cuboid, a hemisphere, a half-ovoid, a frustoconic, another type of polygonal pyramid, or a combination of such shapes or features. The front housing 302 can have an aperture or opening positioned at an apex or fore of the front housing 302. The back housing 304 can be substantially shaped as an open or hollow cuboid having five sides.

Figure 3B:
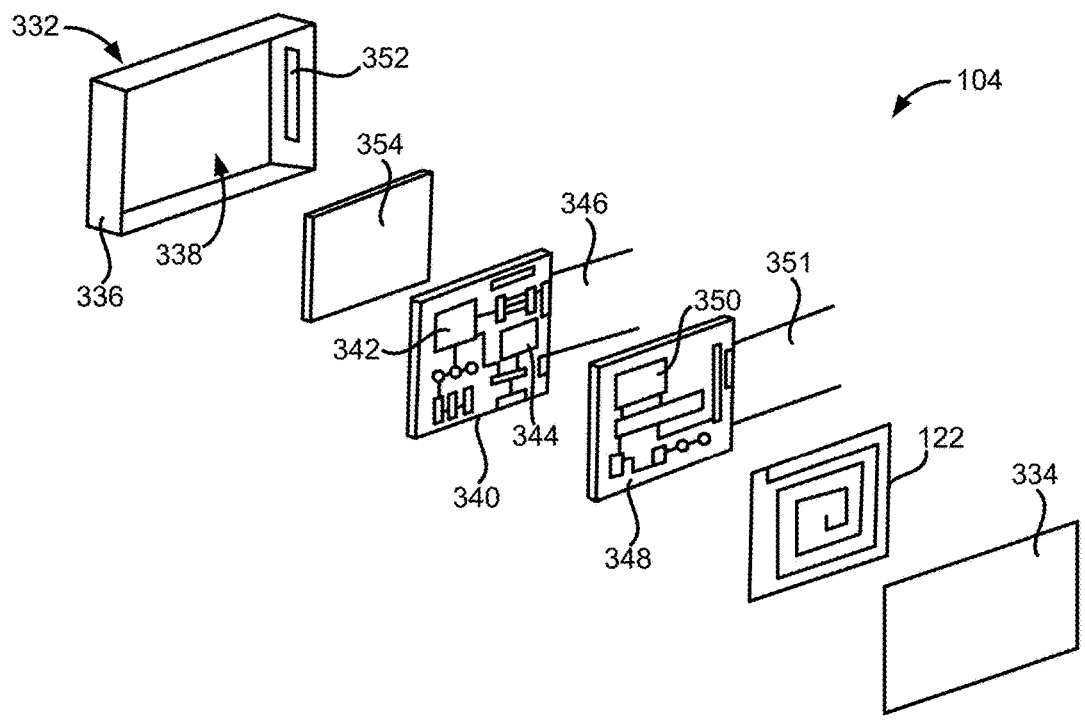
FIG. 3B illustrates an exploded view of an embodiment of an extraocular component of the vision restoration device.

The back housing 304 can also comprise a number of back housing interior walls 308 and the front housing 302 can comprise a number of front housing interior walls (not visible in FIG. 3B). The back housing interior walls 308 and the front housing interior walls can surround the housing cavity 306 when the front housing 302 is coupled to the back housing 304. The back housing interior walls 308 and the front housing interior walls can be coated or covered by a light-sealing coating or paint. The light-sealing coating will be discussed in more detail in the following sections.

The projector 114 can comprise a miniature electronic display 310 and a light emitting component 312 as the primary electronic components. In some embodiments, the electronic display 310 can be a liquid-crystal display (LCD) display. More specifically, the electronic display 310 can be an active matrix liquid-crystal display (AMLCD). The electronic display 310 can display the digital images 116 in color. In some embodiments, the electronic display 310 can have an active pixel area of about 7.0 mm (length dimension) and 5.0 mm (width dimension). In other embodiments, the length dimension of the active pixel area can range from about 1.0 mm to about 10.0 mm and the width dimension of the active pixel area can range from about 1.0 mm to about 10.0 mm.

In other embodiments contemplated by this disclosure, the electronic display 310 can also be a liquid crystal on silicon (LCoS) display, a light-emitting diode (LED) display, an organic light-emitting diode (OLED) display, or an active-matrix organic light-emitting diode (AMOLED) display. In some of these embodiments, the projector 114 can operate without at least one of the polarizing filters.

The electronic display 310 can be coupled to a display wire 314. The display wire 314 can be one or more of the conductive wires making up the trans-scleral communication wire 106. The conductive wires or leads from the display wire 314 (or trans-scleral communication wire 106) can be electrically coupled to circuitry within the electronic display 310. For example, the conductive wires or leads from the display wire 314 (or trans-scleral communication wire 106) can be electrically coupled to inputs along one or more sides or edges of the electronic display 310.

The projector 114 can also comprise a light emitting component 312 comprising a light reflecting enclosure 316 and an LED module 318. The light reflecting enclosure 316 can comprise a number of enclosure interior walls 320. The enclosure interior walls 320 can be covered or coated with a reflective material or coating to reflect light emitted by the LED module 318 in the direction of the electronic display 310. In this manner, the light emitting component 312 can act as a backlight to illuminate the electronic display 310. At least one of the LED module 318 can be housed within the light reflecting enclosure 316 and secured to the light reflecting enclosure 316 by adhesives, clips, supports, fasteners, or a combination thereof.

The LED module 318 can comprise one or more LEDs. In some embodiments, the LEDs can be OLEDs, microLEDs, or a combination thereof. The one or more LEDs on the LED module 318 can have a power output ranging from about 1 mW to about 200 mW. In one embodiment, the one or more LEDs on the LED module 318 can have a power output of about 50 mW. The LED module 318 can also be coupled to an LED wire 322. The LED wire 322 can be one or more of the conductive wires making up the trans-scleral communication wire 106. The trans-scleral communication wire 106 can be introduced into the housing cavity 306 through a slot 324 or opening defined along an edge or side of the projector housing 300. In one embodiment, the slot 324 or opening can be defined along a side of the back housing 304.

The projector 114 can further comprise a light diffuser 326, a first polarizing filter 328, and a second polarizing filter 330. The light diffuser 326 can be configured to diffuse light emitted by the light emitting component 312. The light diffuser 326 can be a thin polymeric film or panel. In some embodiments, the light diffuser 326 can have a surface feature or surface treatment configured to diffuse light. The light diffuser 326 can be made in part of a medical-grade prismatic acrylic, a medical-grade polycarbonate, or a medical-grade polyethylene terephthalate (PET).

The first polarizing filter 328 can be positioned in between the electronic display 310 and the front housing interior wall. The second polarizing filter 330 can be positioned in between the light diffuser 326 and the electronic display 310. In this manner, the electronic display 310 can be sandwiched or set in between the two polarizing filters. The first polarizing filter 328 can have a different polarization orientation (e.g., vertical polarization) than the second polarizing filter 330 (e.g., horizontal polarization). For example, the first polarizing filter 328 can have a polarization orientation set at 90° from the polarization orientation of the second polarizing filter 330. The second polarizing filter 330 can polarize light directed at the electronic display 310 (e.g., the LCD display) and the first polarizing filter 328 can filter or block out light not intended to be displayed by the electronic display 310. The various components of the projector 114 can operate to project one or more digital images 116 displayed by the electronic display 310 on the central retina 204 of the subject.

FIG. 3B illustrates an exploded view of an embodiment of an extraocular component 104. In some embodiments, the extraocular component 104 can be configured to be implanted subcutaneously in proximity to an eye or ear of the subject. In other embodiments, the extraocular component 104 can be configured to be implanted on an eye of the subject.

The extraocular component 104 can comprise an extraocular component housing 332 comprising a front extraocular housing 334 and a back extraocular housing 336. The front extraocular housing 334 can be coupled to the back extraocular housing 336 to define an extraocular housing cavity 338. The front extraocular housing 334 can be coupled to the back extraocular housing 336 by adhesives, an interference fit, heat sealing or other polymer welding techniques, or a combination thereof.

The extraocular component 104 can also comprise a control processor module 340 comprising one or more processors coupled to a miniature printed-circuit board (PCB). The one or more processors of the control processor module 340 can comprise a wireless communication processor 342, a display processor 344, or one processor or chip configured to handle both communications and display functions. The one or more processors of the control processor module 340 can be implemented as a 32-bit processor or a 64-bit processor. The one or more processors can also be implemented as a multiple-core processor. In some embodiments, the display processor 344 can be a multiple-core processor such as a graphics processing (GPU) having numerous processor cores.

In some embodiments, the wireless communication processor 342 can be a processor configured to transmit and receive data over a short-range communication protocol such as an Institute of Electrical and Electronics Engineers (IEEE) 802.11 wireless communications standard (e.g., IEEE 802.11ad, IEEE 802.11ac, IEEE 802.11n, etc.). In other embodiments, the communication processor 342 can be a processor configured to transmit and receive data over a Bluetooth™ protocol, a Bluetooth™ Low Energy (BLE) protocol, or a combination thereof.

In certain embodiments, the wireless communication processor 342 can be configured to transmit and receive data over a 60 GHz frequency band (e.g., over a WirelessHD™ communications standard, a WiGig™ communications standard, etc.), a 5 GHz frequency band, a 2.4 GHz frequency band, or a combination thereof. In some embodiments, the wireless communication processor 342 can be a WiFi chip or module, a WirelessHD™ chip or module, a WiGig™ chip or module, a Bluetooth™ chip or module, a Bluetooth™ Low Energy (BLE) chip or module, or a combination thereof.

In additional embodiments, the wireless communication processor 342 can be coupled to the wireless power and data receiver coil 122 (see also FIG. 4B) and can receive data using the wireless power and data receiver coil 122 over a near-field communication (NFC) protocol. In these embodiments, the wireless power and data receiver coil 122 can serve as a communication antenna as well as a wireless power receiver.

In certain embodiments, the wireless communication processor 342 can also be used to control the electronic display 310, the LED module 318, or a combination thereof. In other embodiments, a separate display processor 344 can be used to control the electronic display 310, the LED module 318, or a combination thereof. The display processor 344, the wireless communication processor 342, or a combination thereof can be programmed to execute instructions stored in a memory unit or memory component coupled to the control processor module 340 to receive the one or more digital images 116 from an extracorporeal device 1000 (see FIGS. 10A, 10B and 10C) and store the one or more digital images 116 in the memory unit or memory component. The display processor 344, the wireless communication processor 342, or a combination thereof can also instruct the projector 114 to project the one or more digital images 116 onto the central retina 204 of the subject.

The control processor module 340 can also be coupled to a data transmission wire 346. The data transmission wire 346 can be part of the trans-scleral communication wire 106. For example, the data transmission wire 346 can be one or more of the conductive wires making up the trans-scleral communication wire 106. The data transmission wire 346 can allow the control processor module 340 to be connected to the LED module 318 and the electronic display 310 of the intraocular projection component 102.

Figure 10A:
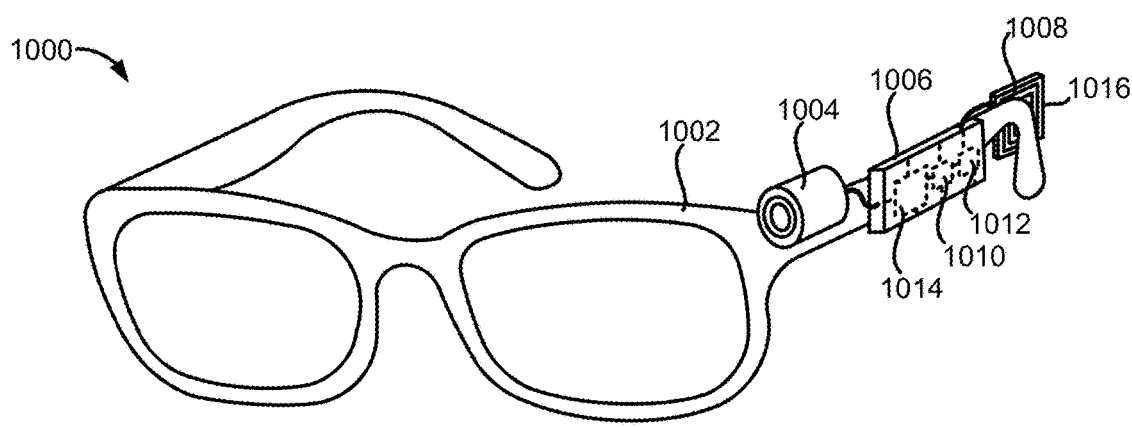
FIG. 10A illustrates one embodiment of an extracorporeal device.
Figure 10B:
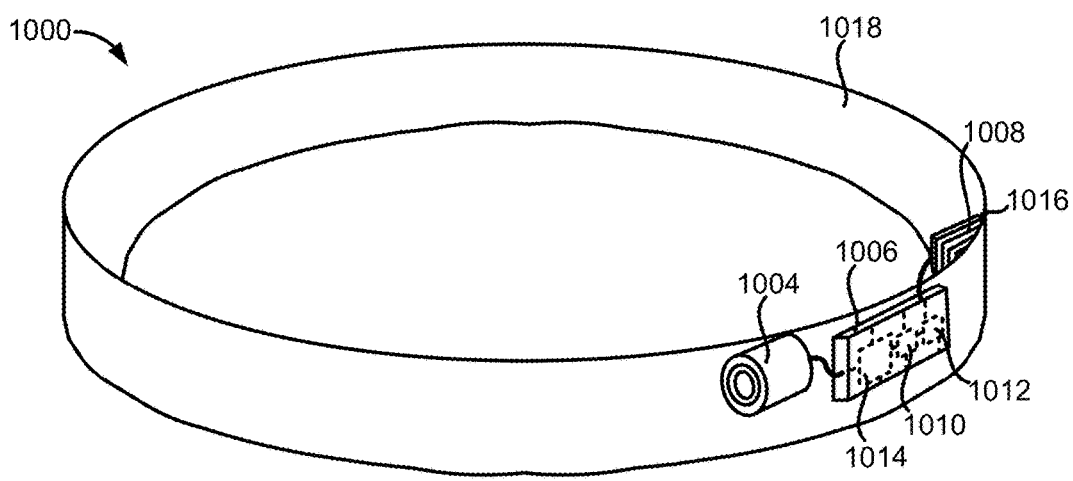
FIG. 10B illustrates another embodiment of an extracorporeal device.

The extraocular component 104 can also comprise a wireless power and data receiver coil 122 (see also FIG. 4B) configured to receive power wirelessly from a wireless power and data transmitter coil 1008 (see FIGS. 10A and 10B). As will be discussed in more detail in the following sections, the wireless power and data transmitter coil 1008 can be part of an extracorporeal device 1000 configured to be worn by the subject.

The extraocular component 104 can further comprise a power module 348 comprising one or more coil processors 350. The power module 348 can comprise converters, rectifiers, or other electronic components needed to convert power received via the wireless power and data receiver coil 122 into a form usable by the electronic components of the extraocular component 104 and the intraocular projection component 102. The coil processors 350 can be configured to manage the components of the power module 348.

The power module 348 can also be coupled to a power transmission wire 351. The power transmission wire 351 can be part of the trans-scleral communication wire 106. The power transmission wire 351 can be configured to deliver power to the electronic components within the intraocular projection component 102. Although FIG. 3B illustrates the data transmission wire 346 and the power transmission wire 351 as two separate wires, it is contemplated by this disclosure and it should be understood by one of ordinary skill in the art that the wires can be combined into one conductive wire or separate portions or segments of the same conductive wire.

The data transmission wire 346 and the power transmission wire 351 can be introduced into the extraocular housing cavity 338 through an opening 352 or slot defined along an edge or side of the extraocular component housing 332. In one embodiment, the opening 352 or slot can be defined along a side of the back extraocular housing 336.

The extraocular component 104 can also comprise a rechargeable battery 354 housed within the extraocular component housing 332. The rechargeable battery 354 can be recharged by power received wirelessly via the wireless power and data receiver coil 122. The rechargeable battery 354 can allow the vision restoration device 100 to still provide visual function to the subject when the wireless power and data transmitter coil 1008 (e.g., the extracorporeal device 1000 comprising the wireless power and data transmitter coil 1008) is not in proximity to the extraocular component 104.

Figure 4A:
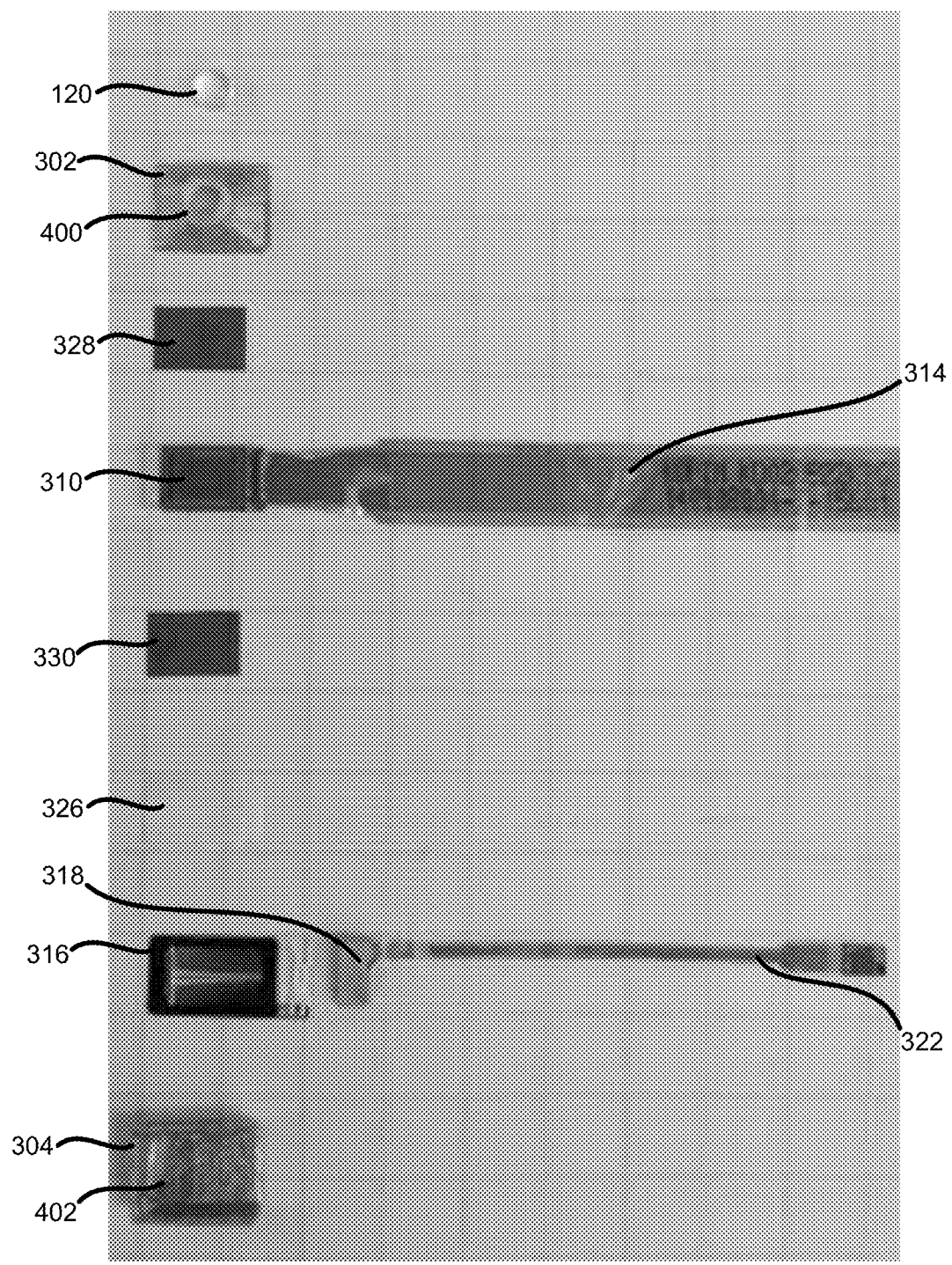
FIG. 4A is a black-and-white image of the intraocular projection component in a disassembled state.

FIG. 4A is a black-and-white image of the intraocular projection component 102 in a disassembled state. As shown in FIG. 4A, the intraocular projection component 102 can comprise at least one lens 120 coupled to a portion of the projector housing 300 such as the front housing 302 of the projector 114.

In some embodiments, the lens 120 can be housed within a projector shroud 400 extending out from the front housing 302. In one embodiment, the projector shroud 400 can be substantially shaped as a hollow cylinder. The projector shroud 400 can be configured to secure the lens 120 and protect the lens 120 from damage. In some embodiments, the lens 120 can be configured to translate in an anterior direction, a posterior direction, or a combination thereof when housed within the projector shroud 400. As will be discussed in more detail in the following sections, the lens 120 can be housed within an adjustable lens housing 610 (see FIG. 6C) and the adjustable lens housing 610 can be coupled to the projector shroud 400 via a threaded or screw-on connection.

The projector housing 300 (including the front housing 302 and the back housing 304) can be made in part of a biocompatible polymeric material. In some embodiments, the projector housing 300 can be made in part of at least one of medical grade poly(methyl methacrylate) (PMMA), medical grade silicone, and medical grade polyvinyl chloride (PVC). In other embodiments, the projector housing 300 can be made in part of a ceramic material.

FIG. 4A also illustrates that the interior walls of the front housing 302 and the back housing 304 is coated by a light-sealing coating 402. In one embodiment, the light-sealing coating 402 can be a silver-colored or silver-pigmented coating or paint. In another embodiment, the light-sealing coating 402 can be a black-colored or black-pigmented coating or paint. More specifically, the light-sealing coating 402 can be an acrylic paint, metallic paint, or a combination thereof.

Figure 4B:
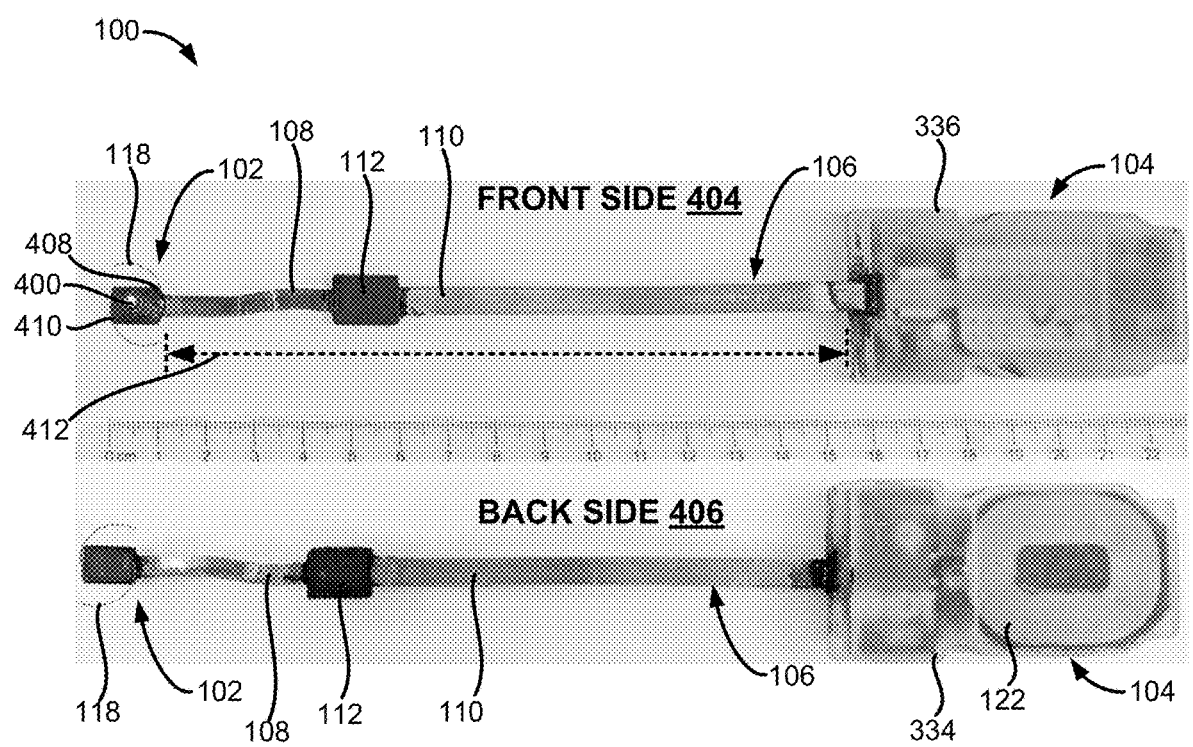
FIG. 4B is a black-and-white image showing a front and back side of one embodiment of the vision restoration device in an assembled state.

FIG. 4B is a black-and-white image showing a front side 404 and a back side 406 of one embodiment of the vision restoration device 100 in an assembled state. As shown in FIG. 4B, the securing haptics 118 can be a set of scleral haptics shaped as spiral or curved arms. The scleral haptics can be a set of polymeric filaments or wires positioned at diagonal or opposite corners or sides of the projector housing 300. For example, as seen in FIG. 4B, one of the scleral haptic arms can be positioned at a first housing corner 408 of the projector housing 300 and another of the scleral haptic arms can be positioned at a second housing corner 410 diagonal to the first housing corner 408. As illustrated in FIG. 4B, the two scleral haptics can delineate a sigmoid-shape or a reverse sigmoid-shape. In other embodiments not shown in FIG. 4B, the securing haptics 118 can be positioned on the top and bottom edges of the projector housing 300, on opposite side edges of the projector housing 300, and along all four corners or sides of the projector housing 300.

FIG. 4B also illustrates that the trans-scleral communication wire 106 can be a substantially flat ribbon-shaped conductive wire. The trans-scleral communication wire 106 can be made in part of one or more conductive wires covered by a biocompatible polymeric material. In some embodiments, at least one of the conductive wires can be made in part of at least one of copper, gold, and silver. The biocompatible polymeric material can be made in part of at least one of medical grade silicone, medical grade thermoplastic elastomers (TPEs), medical grade thermoplastic polyurethanes (TPUs), and medical grade polyvinyl chlorides (PVCs). In other embodiments not shown in the figures, the trans-scleral communication wire 106 can comprise a plurality of intertwined or braided conductive wires. In these embodiments, the trans-scleral communication wire 106 can have a substantially circular transverse cross-section.

In all such embodiments, the trans-scleral communication wire 106 can be flexible and bendable. The flexibility and bendability of the trans-scleral communication wire 106 can allow the intraocular projection component 102 to be implanted within the eye of the subject in a first planar orientation (i.e., a plane bisecting the projector housing 300) and the extraocular component 104 to be implanted in another location within the subject in a second planar orientation (i.e., a plane bisecting the extraocular component housing 332) perpendicular or oblique (i.e., at an acute angle or obtuse angle) to the first planar orientation. For example, the projector 114 can be implanted near the anterior portion 202 of the eye and the one or more lenses 120 of the projector 114 can face the central retina 204. Also in this example, the extraocular component 104 can be implanted subcutaneously near a temple region of the subject along the side of the head of the subject.

As shown in FIG. 4B, the intraocular projection component 102 can be separated from the extraocular component 104 by a separation distance 412 determined by the length of the trans-scleral communication wire 106. In the example embodiment shown in FIG. 4B, the intraocular projection component 102 can be separated from the extraocular component 104 by a separation distance 412 of about 14.5 cm. In other embodiments, the separation distance 412 can range from about 0.5 cm to 30.0 cm. The length of the trans-scleral communication wire 106 (and the size of the trans-scleral communication wire 106) can change based on the separation distance 412. As will be discussed in the following sections, in some embodiments, the extraocular component 104 can be secured to an exterior surface of the eye of the subject, which would result in a shorter trans-scleral communication wire 106.

FIG. 4B also shows that the trans-scleral communication wire 106 can comprise a first wire segment 108 connected to a second wire segment 110 by a wire connector 112. The wire connector 112 can comprise an insulating housing and both a male and female component. The wire connector 112 can allow the first wire segment 108 to be disconnected or detached from the second wire segment 110. The wire connector 112 can be a plug type connector, a multiple-pin type connector, a jack-type connector, a clamp-type connector, or a combination thereof.

As shown in FIG. 4B, the wireless power and data receiver coil 122 can be a low-profile substantially planar coil. The low profile or flatness of the coil can ensure the coil does not unnecessarily add to the depth or thickness of the extraocular component housing 332. Since some sites for implanting the extraocular component 104 involve regions along the side of the head of the subject, any added thickness or depth can make such a component appear unsightly or protruding when implanted subcutaneously.

The wireless power and data receiver coil 122 can receive data, power, or a combination thereof from a compatible transmitter coil (such as, for example, the wireless power and data transmitter coil 1008 of FIGS. 10A and 10B). In some embodiments, the wireless power and data receiver coil 122 can receive data over a near-field communication (NFC) protocol. In these and other embodiments, the wireless power and data receiver coil 122 can receive power based on near-filed electromagnetic coupling with a compatible transmitter coil (such as, for example, the wireless power and data transmitter coil 1008 of FIGS. 10A and 10B). For example, the wireless power and data receiver coil 122 can be a Qi™-compliant wireless receiver coil.

In certain embodiments, the wireless power and data receiver coil 122 can receive data from the wireless power and data transmitter coil 1008 at a data transfer rate ranging from about 1 Megabits per second (Mbps) to about 100 Mbps. For example, the wireless power and data receiver coil 122 can receive data at a data transfer rate of about 10 Mbps. In some embodiments, the wireless power and data receiver coil 122 can receive data from the wireless power and data transmitter coil 1008 via an amplitude-shift keying (ASK) modulation such as on-off keying (OOK).

In some embodiments, the wireless power and data receiver coil 122 can receive power at a rate ranging from about 1 milliwatt (mW) to about 10 W. For example, the wireless power and data receiver coil 122 can receive power at a rate of about 500 mW. More specifically, the wireless power and data transmitter coil 1008 (see, for example, FIGS. 10A and 10B) can supply the wireless power and data receiver coil 122 with a voltage ranging from about 0.1 V to about 10 V (e.g., 5 V) and a current ranging from about 0.01 Amperes (A) to about 1.0 A (e.g., 0.1 A).

Although FIGS. 1, 3B, and 4B show one instance of the wireless power and data receiver coil 122, it is contemplated by this disclosure that multiple coils can be used and certain coils can be dedicated to data transfer while other coils can be dedicated to power transfer. Therefore, any reference to "a" and "the" wireless power and data receiver coil 122 in this disclosure can also refer to wireless power and data receiver coils 122.

The extraocular component housing 332 can be made in part of a biocompatible polymeric material. In some embodiments, the extraocular component housing 332 can be made in part of at least one of a medical grade poly (methyl methacrylate) (PMMA), medical grade silicone, and medical grade polyvinyl chloride (PVC). In other embodiments, the extraocular component housing 332 can be made in part of a ceramic material. In some embodiments, the extraocular component housing 332 can have a length dimension ranging from about 1.0 cm to about 10.0 cm. For example, the extraocular component housing 332 can have a length dimension of about 7.5 cm. The extraocular component housing 332 can also have a width dimension ranging from about 1.0 cm to about 5.0 cm. For example, the extraocular component housing 332 can have a width dimension of about 3.5 cm.

Figure 5A:
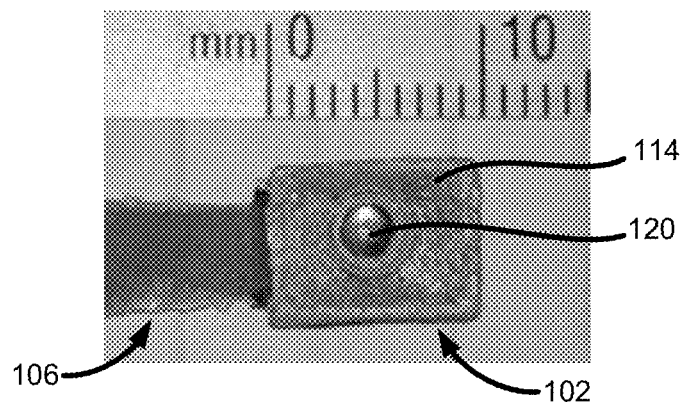
FIGS. 5A to 5C are black-and-white images showing close-ups of one embodiment of the intraocular projection component.
Figure 5B:
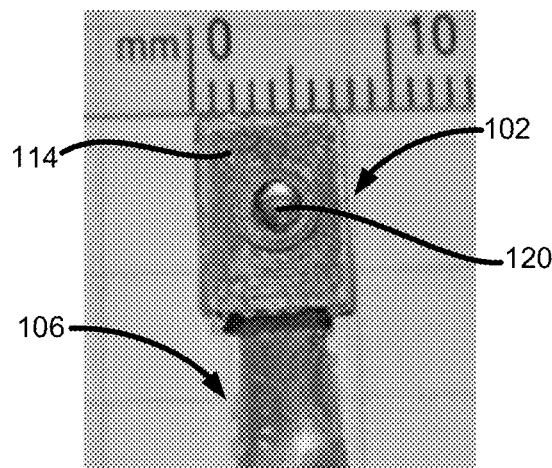
Figure 5C:
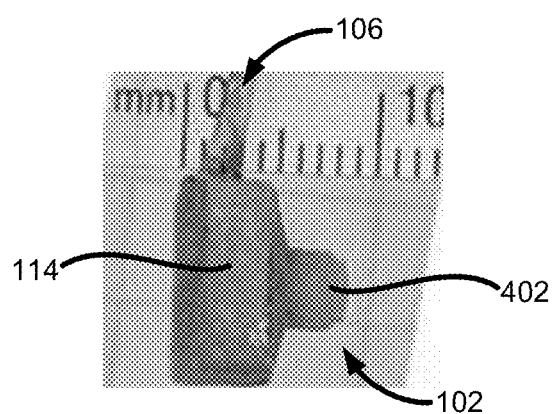

FIGS. 5A to 5C are black-and-white images showing close-ups of one embodiment of the intraocular projection component 102 in an assembled state. As shown in FIG. 5A, the projector 114 of the intraocular projection component 102 can have a length dimension. In one embodiment, the length dimension can be about 10.0 mm. In other embodiments, the length dimension can range from about 1.0 mm to about 11.0 mm.

FIG. 5B shows that the projector 114 can also have a width dimension. In one embodiment, the width dimension can be about 7.0 mm. In other embodiments, the width dimension can range from about 1.0 mm to about 11.0 mm.

FIG. 5C shows that the projector 114 can have a depth dimension as measured from a back side of the back housing 304 of the projector housing 300 to a terminal or distal end of the projector shroud 400. In one embodiment, the depth dimension can be about 9.0 mm. In other embodiments, the depth dimension can range from about 1.0 mm to about 11.0 mm.

Figure 6A:
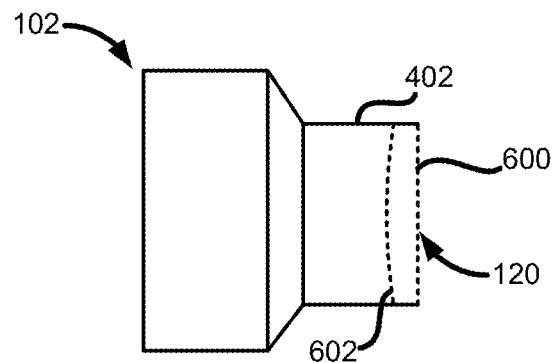
FIG. 6A illustrates a side view of one embodiment of an intraocular projection component having a single lens.

FIG. 6A illustrates a side view of one embodiment of an intraocular projection component 102 having a single lens 120. As shown in FIG. 6A, the single lens 120 can be a plano-convex lens having a substantially planar side 600 and convex side 602. The convex side 602 of the plano-convex lens can be positioned anterior to the substantially planar side 600 when the intraocular projection component 102 is implanted within the eye of the subject. For example, the intraocular projection component 102 can be secured by scleral haptics in the anterior portion 202 of the eye and the front housing 302 of the projector 114 can be pointed or directed at the posterior portion 206 of the eye (e.g., the central retina 204).

In some embodiments, the convex side 602 can have a radius ranging from about 2.0 mm to about 5.0 mm. For example, the convex side 602 can have a radius of about 3.21 mm.

The single lens 120 can be housed within the projector shroud 400. In some embodiments, the single lens 120 can be housed near a distal end of the projector shroud 400. In other embodiments, the single lens 120 can be housed near a proximal end of the projector shroud 400 or in between the proximal end and the distal end of the projector shroud 400.

In other embodiments, the single lens 120 can be a biconvex lens having two convex sides. In these embodiments, the two convex sides can each have a radius ranging from about 2.0 mm to about 5.0 mm.

Figure 6B:
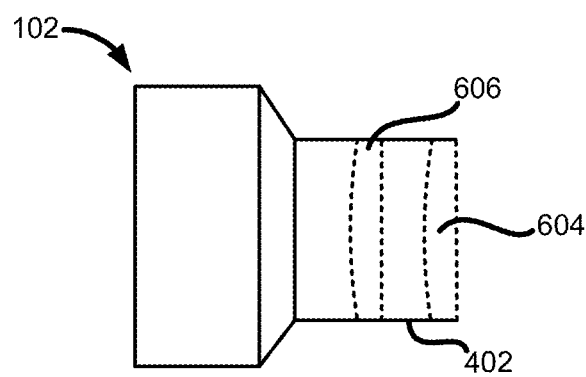
FIG. 6B illustrates a side view of one embodiment of an intraocular projection component having multiple lenses in series.

FIG. 6B illustrates a side view of one embodiment of an intraocular projection component 102 having multiple lenses 120 in series. For example, the multiple lenses 120 in series can be multiple instances of the single lens 120 previously disclosed herein aligned or arranged in series. As shown in FIG. 6B, the intraocular projection component 102 can comprise a first lens 604 and a second lens 606. The first lens 604, the second lens 606, or a combination thereof can each be a plano-convex lens (similar to the single plano-convex lens previously disclosed). In other embodiments, the first lends 604, the second lens 606, or a combination thereof can each be a biconvex lens.

The first lens 604 can be positioned distal to the second lens 606 such that when the intraocular projection component 102 is implanted within the eye of the subject, the second lens 606 is positioned anterior to the first lens 604.

In some embodiments, the lenses 120 used as part of the intraocular projection component 102 (including the single lens 120 and each of the multiple lenses 120) can be a dense flint optical glass lens comprising rare earth elements such as lanthanum(III) oxide ($La_2O_3$). For example, each of the lenses 120 can be made in part of lanthanum-doped silicon dioxide or lanthanum-doped borosilicate glass. In other embodiments, each of the lenses 120 can also comprise lead(II) oxide (PbO), barium oxide (BaO), boron oxide ($B_2O_5$), phosphorus pentoxide ($P_2O_5$), germanium oxide ($GeO_2$), or any combination thereof.

In other embodiments, the lens 120 or lenses 120 used as part of the intraocular projection component 102 can be a clear polymer-based or plastic lens such as an acrylic lens or a silicone lens.

In some embodiments, the single lens 120 or each of the multiple lenses 120 can have an effective focal length (EFL) ranging from about 2.00 mm to about 5.00 mm. For example, the single lens 120 or each of the multiple lenses 120 can have an EFL of about 4.00 mm.

The single lens 120 or each of the multiple lenses 120 can also have a lens diameter and a lens depth dimension. The lens diameter can range from about 1.0 mm to about 10.0 mm and the lens depth dimension can range from about 1.0 mm to about 3.0 mm. For example, the lens diameter can be about 4.00 mm and the lens depth dimension can be about 1.70 mm. The single lens 120 or each of the multiple lenses 120 can also have fine grind surface. The single lens 120 or each of the multiple lenses 120 can be manufactured or distributed by Edmund Scientific Corporation, Schott AG, or other manufacturers or distributers of advanced optical equipment.

Figure 6C:
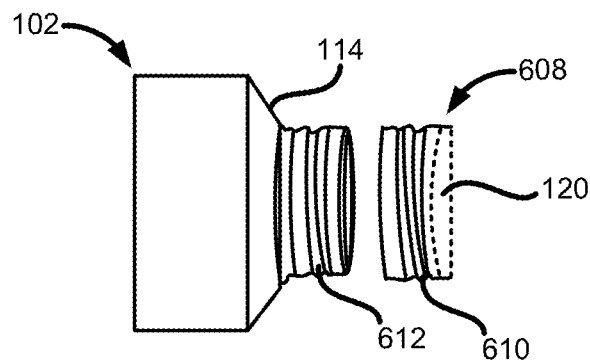
FIG. 6C illustrates a side view of one embodiment of an intraocular projection component having an adjustable lens.

FIG. 6C illustrates a side view of one embodiment of an intraocular projection component 102 having an adjustable lens 608. In this embodiment, the intraocular projection component 102 can comprise an adjustable lens housing 610. The adjustable lens housing 610 can be configured to allow the one or more lenses 120 secured within the adjustable lens housing 610 to translate in an anterior direction, a posterior direction, or a combination thereof relative to the projector 114.

As shown in FIG. 6C, in one embodiment, the projector shroud 400 and the adjustable lens housing 610 can comprise a thread connection 612. The thread connection 612 can allow the adjustable lens housing 610 to be twisted, screwed, or dialed closer or further away from the projector 114. FIG. 6C also illustrates that the one or more lenses 120 secured within the adjustable lens housing 610 can be the plano-convex lenses previously disclosed herein.

In other embodiments, the adjustable lens housing 610 can be translated in an anterior direction, a posterior direction, or a combination thereof using a magnetic mechanism, an electrical mechanism, or a combination thereof.

Figure 7A:
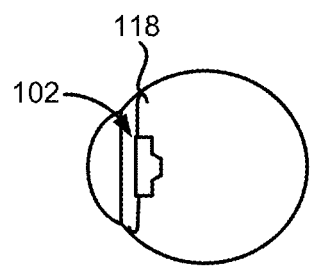
FIGS. 7A to 7D illustrate different ways that the intraocular projection component can be implanted within an eye of a subject.

FIGS. 7A to 7D illustrate different ways that the intraocular projection component 102 can be implanted within an eye of a subject. FIG. 7A illustrates that the intraocular projection component 102 can be secured using two or more securing haptics 118 (e.g., scleral haptics) to the anterior portion 202 of the eye. The securing haptics 118 can be coupled to the projector housing 300 of the intraocular projection component 102. In one embodiment, the subject's own lens capsule 208 (see FIG. 2) can be removed and the intraocular projection component 102 can be secured in a location or position formerly occupied by the lens capsule 208 within the eye of the subject.

Figure 7B:
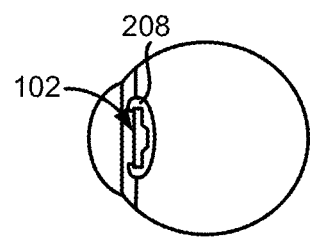

FIG. 7B illustrates that the intraocular projection component 102 can also be implanted within the lens capsule 208 of the eye of the subject. In this embodiment, an incision or opening can be made along a surface of the lens capsule 208 and the intraocular projection component 102 can be positioned within the lens capsule 208 and secured using haptics, sutures, or a combination thereof.

Figure 7C:
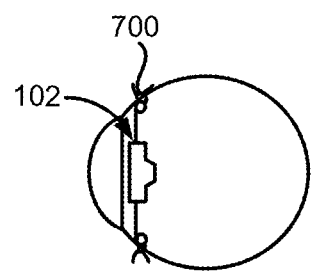

FIG. 7C illustrates that the intraocular projection component 102 can be secured within the eye using sutures 700. For example, the sutures 700 can be coupled to suture openings defined on two or more securing haptics 118 coupled to the projector housing 300 of the intraocular projection component 102. In some embodiments, the sutures 700 can be bioabsorbable sutures, non-bioabsorbable sutures, or a combination thereof. For example, the sutures 700 can be made in part of filaments of polyglycolic acid, polylactic acid, poliglycaprone (or a copolymer of glycolide and ε-caprolactone), polydioxanone, nylon, polypropylene, polyester, polyvinylidene fluoride (PVDF), ultra-high molecular weight polyethylene (UHMWPE), or a combination thereof.

Figure 7D:
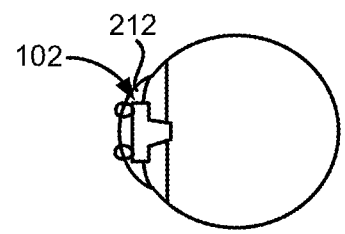

FIG. 7D illustrates that the intraocular projection component 102 can also be implanted within the cornea 212 of the subject. In this embodiment, the intraocular projection component 102 can be secured within the cornea 212 using one or more securing haptics 118, sutures 700, or a combination thereof.

Figure 8A:
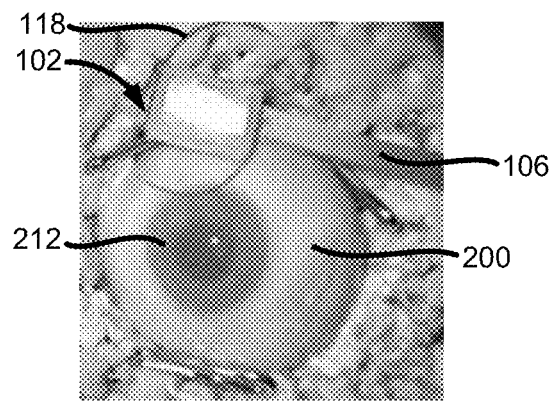
FIGS. 8A to 8C are black-and-white images showing the implantation of one embodiment of the intraocular projection component within an eye of the subject.
Figure 8B:
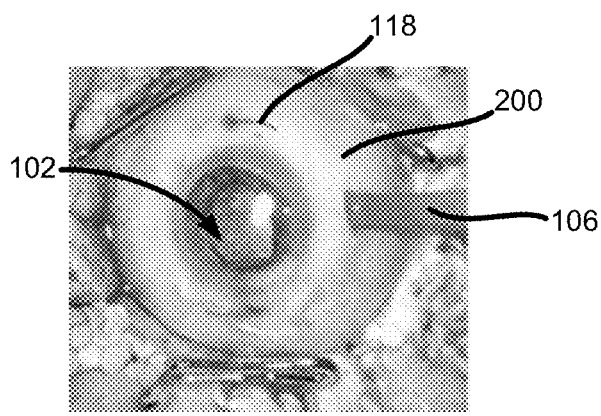
Figure 8C:
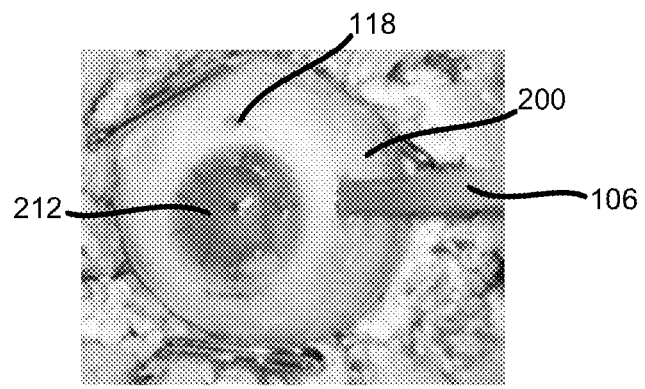

FIGS. 8A to 8C are black-and-white images showing the implantation of one embodiment of the intraocular projection component 102 within an eye of the subject. The cornea 212 of the subject can be removed and one or more incisions can be made along the sclera 200 of the eye to allow the trans-scleral communication wire 106 to pass through. In the embodiment shown in FIG. 8A, the intraocular projection component 102 can comprise a pair of scleral haptics coupled to the projector housing 300. Once the cornea 212 is removed (see FIG. 8B) the intraocular projection component 102 can be secured to the anterior portion 202 of the eye using the scleral haptics. The terminal ends of the scleral haptics can also be cauterized or heat treated to facilitate the securement of the scleral haptics and prevent the scleral haptics from inadvertently retracting out of the sclera. Once the intraocular projection component 102 is secured within the eye, the cornea 212 of the subject can be sewn back onto the eye using sutures (as shown in FIG. 8C). In other embodiments, a replacement cornea (e.g., a donated cornea) or an artificial cornea can be sewn onto the eye of the subject rather than the subject's own cornea.

Figure 9:
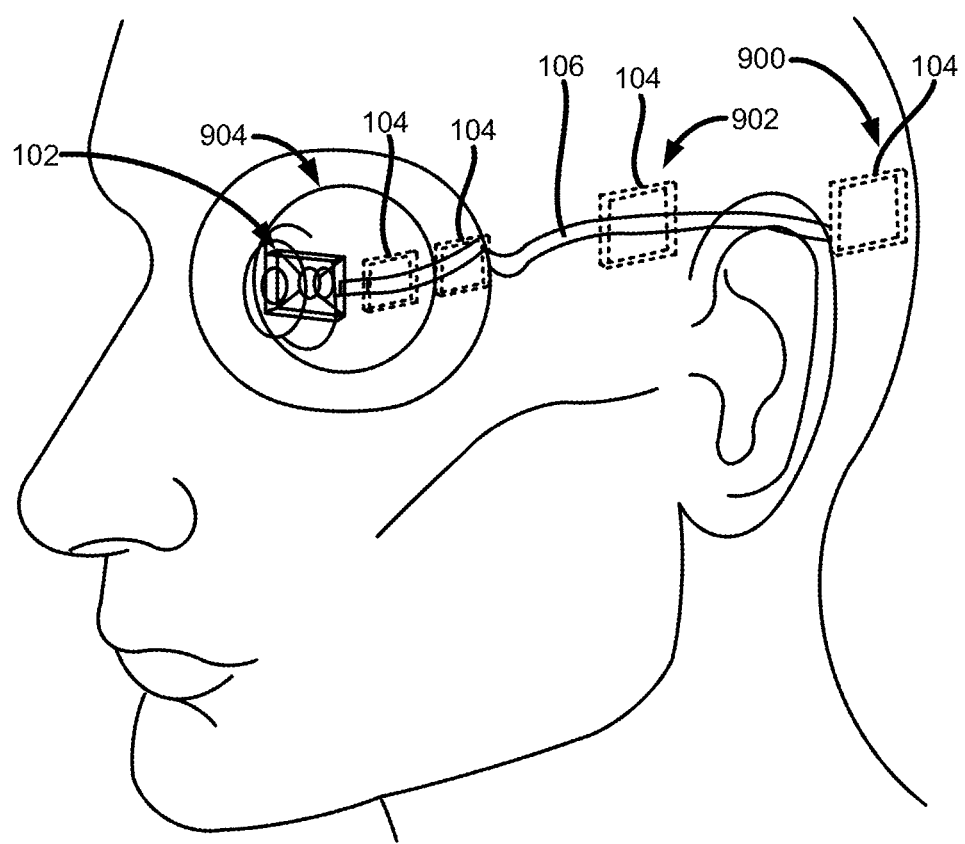
FIG. 9 illustrates various implantation sites for the extraocular component.

FIG. 9 illustrates various implantation sites for the extraocular component 104. In one embodiment, the extraocular component 104 can be implanted subcutaneously in a retroauricular region 900 (e.g., in a region behind the ear) of the subject. In another embodiment also shown in FIG. 9, the extraocular component 104 can be implanted subcutaneously in proximity to a temple region 902 (an area overlying the temporal bone and part of the sphenoid bone) of the subject. In these embodiments, the extraocular component 104 can be implanted subcutaneously at a depth between about 1.0 mm to about 10.0 mm below the skin surface. The extraocular component 104 can be sutured upon implantation to secure the extraocular component 104 or scar tissue can be allowed to form around the extraocular component 104 to secure the extraocular component 104 in place under the skin.

In additional embodiments shown in FIG. 9, the extraocular component 104 can be implanted within an orbit 904 of the subject or along an orbital rim of the subject. In yet another embodiment, the extraocular component 104 can be secured on an exterior surface of the eye. For example, the extraocular component 104 can be coupled to a band or loop strapped to the exterior surface of the eye. The extraocular component 104 can also be sutured to the eye.

FIG. 10A illustrates one embodiment of an extracorporeal device 1000 comprising a wearable support structure 1002, a digital camera 1004, a processor housing 1006, and a wireless power and data transmitter coil 1008. The wearable support structure 1002 can be configured to be worn in proximity to the eyes of the subject. For example, as shown in FIG. 10A, the wearable support structure 1002 can be an eyeglass frame comprising two eyeglass rims connected by a bridge, a pair of nose pads coupled to the eyeglass rims, frame arms or temples coupled to the eyeglass rims by hinges and fasteners, and an earpiece or end tip coupled to each of the frame arms or temples.

The digital camera 1004 can be coupled to the wearable support structure 1002. For example, the digital camera 1004 can be coupled to the frame arms or temples of an eyeglass frame serving as the wearable support structure 1002. In other embodiments, the digital camera 1004 can be coupled to part of the eyeglass rims or the bridge. The digital camera 1004 can be configured to capture the one or more digital images 116 projected by the projector 114 of the intraocular projection component 102.

In one embodiment, the digital camera 1004 can be a Full HD (FHD) camera configured to capture 1080p video (e.g., 1080p24, 1080p25, 1080p25, 1080p30, or 1080p60 video and a 16:9 aspect ratio). In this embodiment, the digital camera 1004 can capture video with a resolution of about 1920×1080 pixels and static images at 3280×2464 pixels. In other embodiments, the digital camera 1004 can be a standard HD camera configured to capture 720p video at a resolution of about 1280×720 pixels. In additional embodiments contemplated by this disclosure, the digital camera 1004 can be a Quad HD (QHD) camera configured to capture 1440p video (2560×1440 pixels). In further embodiments contemplated by this disclosure, the digital camera 1004 can be a 4K Ultra HD (UHD) camera configured to capture 2160p video (or a resolution of about 4096×2160 pixels). In additional embodiments contemplated by this disclosure, the digital camera 1004 can be an 8K UHD camera configured to capture 4230p video (or a resolution of about 7680×4320 pixels).

In alternative embodiments, the digital camera 1004 can be a camera configured to capture images outside the visible spectrum. For example, in one embodiment, the digital camera 1004 can be an infrared, near infrared, or thermal imaging camera. In another embodiment, the digital camera 1004 can be configured to capture images using light in the ultraviolet (UV) or near-UV spectrum.

The processor housing 1006 can also be coupled to the wearable support structure 1002 (e.g., on the arm or temple of an eyeglass frame). The processor housing 1006 can comprise a camera processor 1010 having a camera memory and a wireless communication processor 1012 having a communication memory or memory unit. The camera processor 1010 can be electrically coupled to the digital camera 1004.

The camera processor 1010 can be programmed to execute instruction stored in the camera memory to instruct the digital camera 1004 to capture the one or more digital images 116. The wireless communication processor 1012 can be programmed to execute instructions stored in the communication memory or memory unit to wirelessly transmit the one or more digital images 116 to the extraocular component 104.

In some embodiments, the camera processor 1010 can be a digital signal processor (DSP) comprising one or more processor cores. In some embodiments, the camera processor 1010 can be a 1.7 GHz dual core processor or a 1.5 GHz quad core processor. Although the camera processor 1010 and the wireless communication processor 1012 are shown as separate processors, it is contemplated by this disclosure that the camera processor 1010 and the wireless communication processor 1012 can be the same processor in certain embodiments.

In some embodiments, the wireless communication processor 1012 can be a processor configured to transmit and receive data over a short-range communication protocol such as an Institute of Electrical and Electronics Engineers (IEEE) 802.11 wireless communications standard (e.g., IEEE 802.11ad, IEEE 802.11ac, IEEE 802.11n, etc.). In other embodiments, the communication processor 1012 can be a processor configured to transmit and receive data over a Bluetooth™ protocol, a Bluetooth™ Low Energy (BLE) protocol, or a combination thereof. In certain embodiments, the wireless communication processor 1012 can be configured to transmit and receive data over a 60 GHz frequency band (e.g., over a WirelessHD™ communications standard, a WiGig™ communications standard, etc.), a 5 GHz frequency band, a 2.4 GHz frequency band, or a combination thereof. In some embodiments, the wireless communication processor 1012 can be a WiFi chip or module, a WirelessHD™ chip or module, a WiGig™ chip or module, a Bluetooth™ chip or module, a Bluetooth™ Low Energy (BLE) chip or module, or a combination thereof.

In additional embodiments, the wireless communication processor 1012 can be coupled to the wireless power and data transmitter coil 1008 and can transmit data using the wireless power and data transmitter coil 1008 over a near-field communication (NFC) protocol. In these embodiments, the wireless power and data transmitter coil 1008 can serve as a communication antenna as well as a wireless power transmitter.

FIG. 10A illustrates that the processor housing 1006 can also comprise a portable power supply 1014. In other embodiments, the portable power supply 1014 can be housed in a different housing or device casing separate from the processor housing 1006.

In some embodiments, the portable power supply 1014 can be a rechargeable battery. The portable power supply 1014 can be configured to supply power to the digital camera 1004, the camera processor 1010, the wireless communication processor 1012, or a combination thereof. The portable power supply 1014 can also be configured to supply power to the wireless power and data transmitter coil 1008.

The wireless power and data transmitter coil 1008 can be housed within a coil housing 1016 coupled to the wearable support structure 1002. In some embodiments, the coil housing 1016 can be a polymeric container or casing configured to hold the wireless power and data transmitter coil 1008. As shown in FIG. 10A, the coil housing 1016 can be positioned on an inner side or surface of the wearable support structure 1002 (such as an inner side or surface of the frame arm). Positioning the coil housing 1016 on the inner side or surface of the wearable support structure 1002 can allow the wireless power and data transmitter coil 1008 to be positioned more closely or in close proximity to the wireless power and data receiver coil 122 of the extraocular component 104 implanted within the subject. The wireless power and data transmitter coil 1008 can be configured to transmit power wirelessly to the wireless power and data receiver coil 122 to power the electronic components of the extraocular component 104, the intraocular projection component 102, or a combination thereof. In some embodiments, the wireless power and data transmitter coil 1008 can transmit power to the wireless power and data receiver coil 122 to recharge the rechargeable battery 354 within the extraocular component 104. In these embodiments, the electronic components of the extraocular component 104 and the intraocular projection component 102 can draw power from the rechargeable battery 354.

As shown in FIGS. 10A and 10B, the wireless power and data transmitter coil 1008 can be a low-profile substantially planar coil. The low profile or flatness of the coil can ensure the coil does not unnecessarily add to the depth or thickness of the wearable support structure 1002.

The wireless power and data transmitter coil 1008 can transmit data, power, or a combination thereof to a compatible receiver coil (such as, for example, the wireless power and data receiver coil 122 of FIGS. 1, 3B, and 4B). In some embodiments, the wireless power and data transmitter coil 1008 can transmit data over a near-field communication (NFC) protocol. In these and other embodiments, the wireless power and data transmitter coil 1008 can transmit power based on near-filed electromagnetic coupling with a compatible receiver coil (such as, for example, the wireless power and data receiver coil 122 of FIGS. 1, 3B, and 4B). For example, the wireless power and data transmitter coil 1008 can be a Qi™-compliant wireless receiver coil.

In certain embodiments, the wireless power and data transmitter coil 1008 can transmit data to the wireless power and data receiver coil 122 at a data transfer rate ranging from about 1 Megabits per second (Mbps) to about 100 Mbps. For example, the wireless power and data transmitter coil 1008 can transmit data at a data transfer rate of about 10 Mbps. In some embodiments, the wireless power and data transmitter coil 1008 can transmit data to the wireless power and data receiver coil 122 via an amplitude-shift keying (ASK) modulation such as on-off keying (OOK).

In some embodiments, the wireless power and data transmitter coil 1008 can transmit power at a rate ranging from about 1 milliwatt (mW) to about 10 W. For example, the wireless power and data transmitter coil 1008 can transmit power at a rate of about 500 mW. More specifically, the wireless power and data transmitter coil 1008 can supply the wireless power and data receiver coil 122 with a voltage ranging from about 0.1 V to about 10 V (e.g., 5 V) and a current ranging from about 0.01 Amperes (A) to about 1.0 A (e.g., 0.1 A).

Although FIGS. 10A and 10B show one instance of the wireless power and data transmitter coil 1008, it is contemplated by this disclosure that multiple coils can be used and certain coils can be dedicated to data transfer while other coils can be dedicated to power transfer. Therefore, any reference to "a" and "the" wireless power and data transmitter coil 1008 in this disclosure can also refer to wireless power and data transmitter coils 1008.

FIG. 10B illustrates another embodiment of the extracorporeal device 1000 comprising a wearable support structure 1002 in the form of a headband 1018. In some embodiments, the wearable support structure 1002 can be a flexible headband. In other embodiments, the wearable support structure 1002 can be a rigid headband. In one or more embodiments, the flexible headband can be a fabric headband comprising an elastomer (e.g., Spandex, natural rubber, synthetic rubber, or a combination thereof). More specifically, the flexible headband can be made in part of organic materials (e.g., cotton, silk, wool, or a combination thereof), synthetic materials or fabrics (e.g., nylon, polyester, or a combination thereof), or a combination thereof.

In these embodiments, the digital camera 1004, the processor housing 1006 (including the camera processor 1010 and the wireless communication processor 1012), the portable power supply 1014, the coil housing 1016, and the wireless power and data transmitter coil 1008 coupled to the headband 1018 can be the same or substantially the same as the digital camera 1004, the processor housing 1006 (including the camera processor 1010 and the wireless communication processor 1012), the portable power supply 1014, the coil housing 1016, and the wireless power and data transmitter coil 1008 coupled to the eyeglass frame shown in FIG. 10A.

As depicted in FIG. 10B, the coil housing 1016 comprising the wireless power and data transmitter coil 1008 can also be coupled or otherwise affixed to an inner side or surface of the headband 1018. Positioning the coil housing 1016 on the inner side or surface of the headband 1018 can allow the wireless power and data transmitter coil 1008 to be positioned more closely or in close proximity to the wireless power and data receiver coil 122 of the extraocular component 104 implanted within the subject.

Figure 10C:
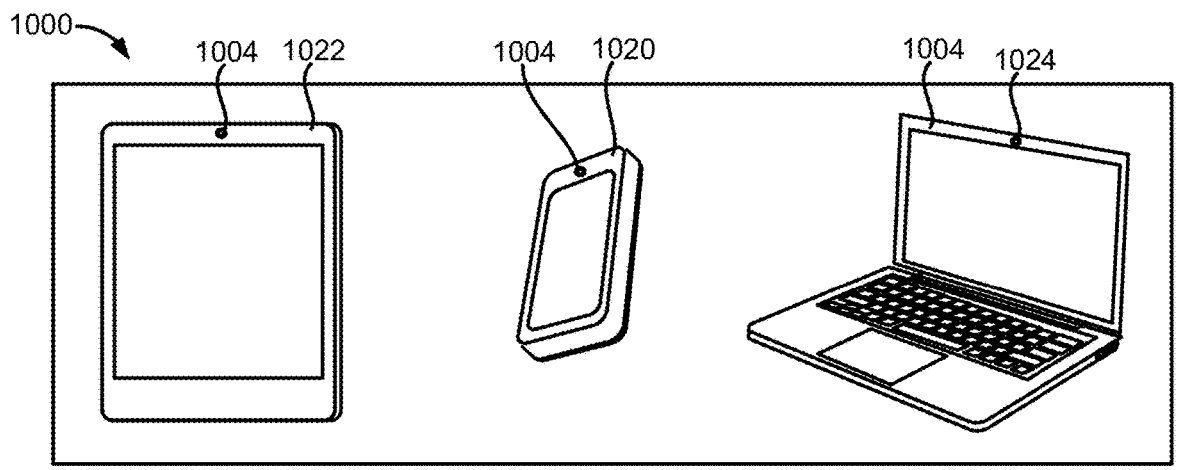
FIG. 10C illustrates additional embodiments of an extracorporeal device.

FIG. 10C illustrates additional embodiments of the extracorporeal device 1000 as portable electronic devices. In one embodiment, the extracorporeal device 1000 can be a smartphone 1020 having a built-in digital camera 1004. In another embodiment, the extracorporeal device 1000 can be tablet computer 1022 having a built-in digital camera 1004. In a further embodiment, the extracorporeal device 1000 can be a laptop 1024 having a built-in digital camera 1004. In these embodiments, the digital cameras 1004 of the portable electronic devices can capture the one or more digital images 116 and save the one or more digital images 116 to a memory of the portable electronic device. The portable electronic device can then wireless transmit the one or more digital images 116 to the extraocular component 104 implanted within the subject over a short-range communication protocol (e.g., WiFi, Bluetooth™, WiGig™, WirelessHD™, or a combination thereof). The extraocular component 104 can then transmit the one or more digital images 116 to the intraocular projection component 102 to be projected onto the central retina 204 of the subject. In these embodiments, the wireless power and data transmitter coil 1008, the portable power supply 1014, or a combination thereof can be housed within a separate portable device or housing. The subject or an operator/user can bring the separate portable device comprising the wireless power and data transmitter coil 1008 in proximity to the extraocular component 104 implanted within the subject to deliver power wirelessly to the extraocular component 104, the intraocular projection component 102, or a combination thereof.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A vision restoration device, comprising:
an intraocular projection component configured to be implanted within an eye of a subject and comprising:
a projector configured to project one or more digital images onto a central retina of the subject, wherein the projector comprises an electronic display housed within a projector housing and a light emitting component, wherein the electronic display is configured to display the one or more digital images, wherein the projector housing further comprises interior housing walls, wherein the interior housing walls surround a housing cavity, and wherein the interior housing walls are coated by a light-sealing coating, and wherein the light emitting component is configured to generate and direct light at the electronic display, and
one or more lenses coupled to or housed within the projector and configured to focus the one or more digital images; and
an extraocular component configured to be implanted within the subject, the extraocular component comprising:
one or more processors programmed to execute instructions stored in a memory to wirelessly receive the one or more digital images from an extracorporeal device; and
a trans-scleral communication wire connecting the intraocular projection component to the extraocular component, wherein the trans-scleral communication wire is configured to transmit digital data between the extraocular component and the intraocular projection component.

2. A vision restoration device, comprising:
an intraocular projection component configured to be implanted within an eye of a subject and comprising:
a projector configured to project one or more digital images onto a central retina of the subject,
wherein the projector comprises:
a projector housing comprising a front housing interior wall and a back housing interior wall;
an electronic display housed within the projector housing and configured to display the one or more digital images;
a first polarizing filter positioned in between the electronic display and the front housing interior wall within the projector housing;
a light emitting component configured to generate and direct light at the electronic display, wherein at least part of the light emitting component is housed within the projector housing;
a light diffuser configured to diffuse the light produced by the light emitting component, wherein the light diffuser is housed within the projector housing; and
a second polarizing filter positioned in between the light diffuser and the electronic display within the projector housing;

one or more lenses coupled to or housed within the projector and configured to focus the one or more digital images; and an extraocular component configured to be implanted within the subject, the extraocular component comprising:
one or more processors programmed to execute instructions stored in a memory to wirelessly receive the one or more digital images from an extracorporeal device; and
a trans-scleral communication wire connecting the intraocular projection component to the extraocular component, wherein the trans-scleral communication wire is configured to transmit digital data between the extraocular component and the intraocular projection component.

3. The vision restoration device of claim 1, wherein at least one of the one or more lenses is a plano-convex lens having a convex side and a planar side, and wherein the convex side is positioned anterior to the planar side such that the convex side is positioned further away from the retina of the subject than the planar side when the intraocular projection component is implanted within the eye of the subject.

4. The vision restoration device of claim 1, wherein the intraocular projection component comprises two or more lenses and the two or more lenses are positioned in series.

5. The vision restoration device of claim 1, wherein at least one of the one or more lenses is an adjustable lens such that the adjustable lens is translatable relative to the projector.

6. The vision restoration device of claim 1, wherein the intraocular projection component further comprises two or more scleral haptics coupled to the projector, wherein the scleral haptics are configured to secure the intraocular projection component to a sclera of the subject.

7. The vision restoration device of claim 1, wherein the extraocular component comprises a wireless power and data receiver coil, wherein the wireless power and data receiver coil is configured to receive power wirelessly from an extracorporeal wireless power and data transmitter coil positioned in proximity to the wireless power and data receiver coil.

8. The vision restoration device of claim 1, wherein the trans-scleral communication wire comprises a first wire segment coupled to the intraocular projection component, a second wire segment coupled to the extraocular component, and a wire connector connecting the first wire segment to the second wire segment, wherein the wire connector is configured to allow the first wire segment to be detached from the second wire segment.

9. The vision restoration device of claim 1, wherein the light emitting component is a light reflecting enclosure housing one or more light-emitting diodes (LEDs).

10. The vision restoration device of claim 1, wherein the electronic display is a liquid-crystal display (LCD).

11. Vision restoration system, comprising:
an extracorporeal device, comprising:
a wearable support structure configured to be worn by a subject,
a digital camera coupled to the wearable support structure,
a housing comprising a camera processor and a wireless communication processor, wherein the camera processor is programmed to execute instructions stored in a camera memory to instruct the digital camera to capture one or more digital images,
a portable power supply, and
a wireless power and data transmitter coil housed within a coil housing coupled to the wearable support structure, wherein the wireless power and data transmitter coil is electrically coupled to the portable power supply;
an extraocular component configured to wirelessly receive the one or more digital images from the extracorporeal device, wherein the extraocular component is configured to be implanted within the subject, and wherein the extraocular component comprises a wireless power and data receiver coil configured to receive power wirelessly via the wireless power and data transmitter coil;
an intraocular projection component configured to be implanted within an eye of the subject and comprising:
a projector configured to project the one or more digital images received by the extraocular component onto a central retina of the subject, wherein the projector comprises an electronic display housed within a projector housing and a light emitting component, wherein the projector housing further comprises interior housing walls, wherein the interior housing walls surround a housing cavity, and wherein the interior housing walls are coated by a light-sealing coating, wherein the electronic display is configured to display the one or more digital images, and wherein the light emitting component is configured to generate and direct light at the electronic display, and
one or more lenses coupled to or housed within the projector configured to focus the one or more digital images; and
a trans-scleral communication wire connecting the extraocular component to the intraocular projection component, wherein the trans-scleral communication wire is configured to transmit digital data between the extraocular component and the intraocular projection component.

12. The vision restoration system of claim 11, wherein the wearable support structure is at least one of an eyeglass frame and a headband.

13. The vision restoration system of claim 11, wherein at least one of the one or more lenses is a plano-convex lens having a convex side and a planar side, and wherein the convex side is positioned anterior to the planar side such that the convex side is positioned further away from the retina of the subject than the planar side when the intraocular projection component is implanted within the eye of the subject.

14. The vision restoration system of claim 11, wherein the light emitting component is a light reflecting enclosure housing one or more light-emitting diodes (LEDs).

15. The vision restoration system of claim 11, wherein the projector further comprises:
a first polarizing filter positioned within the projector housing in between the electronic display and a front housing interior wall of the projector housing;
a light diffuser configured to diffuse the light produced by the light emitting component, wherein the light diffuser is housed within the projector housing; and
a second polarizing filter positioned in between the light diffuser and the electronic display within the projector housing.

16. The vision restoration device of claim 1, wherein the one or more processors of the extraocular component are programmed to control the electronic display and the light emitting component.

17. The vision restoration device of claim 1, wherein the extraocular component is configured to be implanted subcutaneously in a temple region or a retroauricular region of the subject.

18. The vision restoration device of claim 1, wherein the projector further comprises a light diffuser configured to diffuse the light produced by the light emitting component, wherein the light diffuser is housed within the projector housing.

* * * * *

UNITED STATES PATENT AND TRADEMARK OFFICE
CERTIFICATE OF CORRECTION

| | |
|---|---|
| PATENT NO. | : 11,376,163 B2 |
| APPLICATION NO. | : 16/810603 |
| DATED | : July 5, 2022 |
| INVENTOR(S) | : Charles Yu et al. |

It is certified that error appears in the above-identified patent and that said Letters Patent is hereby corrected as shown below:

In the Specification

On Column 1, Line 14, before the "TECHNICAL FIELD", please insert the following paragraph:
--FEDERALLY SPONSORED RESEARCH
This invention was made with government support under contract number W81XWH-19-1-0542 awarded by the Defense Health Agency/Medical Research and Development Branch. The government has certain rights in this invention.--

Signed and Sealed this
Fifteenth Day of October, 2024

Katherine Kelly Vidal
*Director of the United States Patent and Trademark Office*